(12) United States Patent
Büchs

(10) Patent No.: US 8,268,611 B2
(45) Date of Patent: Sep. 18, 2012

(54) MICROTITER PLATE AND USE THEREOF

(75) Inventor: Jochen Büchs, Aachen (DE)

(73) Assignee: RWTH Aachen, Aachen (DE)

( * ) Notice: Subject to any disclaimer, the term of this patent is extended or adjusted under 35 U.S.C. 154(b) by 733 days.

(21) Appl. No.: 12/302,406

(22) PCT Filed: May 21, 2007

(86) PCT No.: PCT/EP2007/004493
§ 371 (c)(1),
(2), (4) Date: Nov. 25, 2008

(87) PCT Pub. No.: WO2007/137722
PCT Pub. Date: Dec. 6, 2007

(65) Prior Publication Data
US 2009/0170183 A1 Jul. 2, 2009

(30) Foreign Application Priority Data

May 26, 2006 (DE) .......................... 10 2006 025 011

(51) Int. Cl.
*C12M 1/00* (2006.01)
*C12N 5/02* (2006.01)
(52) U.S. Cl. ............... 435/283.1; 435/288.2; 435/288.5; 435/382; 435/383
(58) Field of Classification Search .................... None
See application file for complete search history.

(56) References Cited

U.S. PATENT DOCUMENTS

| 5,232,838 | A | * | 8/1993 | Nelson et al. ................... 435/30 |
| 5,422,270 | A | | 6/1995 | Caspi |
| 5,972,694 | A | * | 10/1999 | Mathus ....................... 435/288.4 |
| 6,627,406 | B1 | | 9/2003 | Singh |
| 2002/0168757 | A1 | | 11/2002 | Kirk |
| 2003/0034306 | A1 | | 2/2003 | Schulte |
| 2003/0215941 | A1 | * | 11/2003 | Campbell et al. ............. 435/325 |
| 2005/0089993 | A1 | | 4/2005 | Boccazzi |
| 2005/0260745 | A1 | * | 11/2005 | Domansky et al. ........ 435/294.1 |

FOREIGN PATENT DOCUMENTS
WO WO 2007008609 * 1/2007
* cited by examiner

*Primary Examiner* — Betty Forman
(74) *Attorney, Agent, or Firm* — Lucas & Mercanti, LLP

(57) ABSTRACT

The invention relates to a microtiter plate and use thereof for conducting fermentation under fed-batch conditions. In order to produce a microtiter plate which permits screening under fed-batch conditions, the invention proposes that the cavities (2) of the microtiter plate according to the invention be filled with a culturing fluid and nutrient solution and be designed in such a way that each of the cavities (2) of the microtiter plate which is filled with nutrient solution is connected by a channel (4) to at least one other further cavity (3) of the microtiter plate which is filled with a culturing fluid. A diffusion barrier (13) arranged in the material permeable channel (4) controls the kinetics of the material transfer of nutrients from the cavity containing the nutrient solution to the cavities containing the culturing fluid.

22 Claims, 6 Drawing Sheets

MICROTITER PLATE AND USE THEREOF

PRIORITY CLAIM

This is a U.S. national stage of application No. PCT/EP2007/004493, filed on 21 May 2007. Priority is claimed on the following application: Country: Germany, Application No.: 10 2006 025 011.7, Filed: 26 May 2006, the content of which is/are incorporated here by reference.

BACKGROUND OF THE INVENTION

The invention pertains to a microtiter plate with a plurality of cavities, each of which comprises an opening in the flat top surface. The invention also pertains to the use of a microtiter plate of this type for conducting fermentations.

Known designs have, for example, a frame with a plate, on which a plurality of vessels, which form the receptacles, is mounted. These vessels project from the bottom surface of the plate, and their openings are accessible from the top surface of the plate. Standard microtiter plates can have 24, 48, 96, 384, or even 1,536 cavities arranged in rows and columns.

U.S. Pat. No. 6,018,388 discloses a microtiter plate with a bottom plate and a cavity plate with hollow cylindrical passages, where the bottom plate and the cavity plate are connected to each other in a fluid-tight manner.

Microtiter plates are used for various types of microbiological and immunological processes. They are used in particular for the screening of industrial bioreactions conducted as batch processes. Microtiter plates also offer the considerable advantage that they can be handled by laboratory robots in a completely automated manner.

For industrial bioreactions (fermentations) for production purposes, however, it has been found that fed-batch processes are advantageous. This is the name given to processes in which additional nutrients are supplied. The addition of the nutrients during the course of fermentation usually improves growth and the production output in comparison with pure batch processes.

The growth of microorganisms depends strongly on the composition of the culture liquid, i.e., especially on the composition of the nutrients present in the liquid. If, for example, inhibition occurs as a result of an excess of nutrients; if there is not enough water activity (that is, if the osmotic pressure is too high); if catabolite repression occurs; or if an overflow mechanism begins during the fermentation, it will be impossible to find the optimal microorganisms and culture conditions by batch-method fermentation.

One of the goals of fed-batch processes is in many cases to keep, for a certain period of time, the concentration of limiting nutrients in the reaction vessel or the concentration of a precursor in a low concentration range found to be advantageous for the biological reaction. Another goal of fermentation in the fed-batch process can be simply to grow the microorganisms in a first phase and then, in a second phase, to convert the substance in question into the desired product by adding specific nutrients.

The fed-batch shake-flask technique was developed so that shake flasks can be used for the development of fed-batch processes (Chemie Ingenieur Technik, Vol. 68, 11/96). For this purpose, the simple shake-flask technique was combined with a precise dosing technique adapted to small reaction volumes. The dosing technique makes use of a highly precise piston pump to distribute the various nutrients through a multi-port valve to several shake flasks via dosing lines. The dosing of the nutrients is controlled by a process computer. Thus, by specifying in advance a schedule of the amounts to be dosed over the course of time, it is possible to realize an individual dosing profile for each of the individual shake flasks being operated in parallel. With this fed-batch shake flask system, up to 14 flasks can be supplied with 4 different nutrients.

Although the known fed-batch shake flask system makes it possible for dosing strategies for fed-batch fermentation to be developed and optimized in parallel on a laboratory scale in an automated manner, the number of reaction vessels which can be operated in parallel is limited because of the amount of apparatus required, which is still considerable. It is therefore virtually impossible from an economic standpoint to screen numerous (e.g., several hundred) different microorganisms to find those which provide optimal yields of biomass and/or product.

A testing apparatus for studying cell migration on the basis of chemotaxis, haptotaxis, and chemoinvasion is known from US 2002/0168757. Adjacent wells in a plate of the testing apparatus are connected to each other in pairs by channels. Chemotaxis means the influence which concentration gradients of a substance exert on the direction of movement of living organisms or of the cells of living organisms. Chemoinvasion is defined as the movement of cells in or through a barrier or gel matrix. To study chemotaxis and chemoinvasion, a gel matrix can be placed in the connecting channels between the wells. The gel contains a large amount of water and is porous enough to allow the cells to migrate for chemotaxis or chemoinvasion. The diameter of the connecting channel is approximately the same as that of the cells being studied.

US 2004/0077075 A1 discloses a microfermenter with at least one culture vessel with a volume of less than 1 mL. In a preferred embodiment of the microfermenter, the reaction vessels are connected by channels, through which culture liquid and possibly nutrients are supplied to the reactor under batch-mode operating conditions. The channels are supplied by robots, which take up materials from a microtiter plate, for example, and introduce them into the fermenter. The channels themselves are connected to microfluidic devices, especially pumps.

Another exemplary embodiment of the microfermenter according to US 2004/0077075 A1 comprises two chambers, which are arranged vertically one above the other and which are separated from each other by a membrane. Via the membrane, oxygen and water enter the culture liquid from the lower chamber. A pump, for example, is used to produce circulation in one of the chambers. Insofar as the membrane between the two chambers is also permeable to nutrients, it is also possible to conduct continuous fermentations or fermentations in semi-batch mode. In the case of semi-batch operation, some of the cell culture is harvested after a certain period of time. In the usual case, 70-90% is harvested, and the bioreactor is filled with fresh medium. This cycle is then repeated. This operating mode is not comparable to a fed-batch operating mode. Proceeding from this prior art, the invention is based on the goal of creating a microtiter plate which allows the screening of strains, media, or products under fed-batch conditions and makes possible the development and optimization of dosing strategies for fed-batch fermentations with only modest requirements in terms of apparatus. In addition, the use of the microtiter plate for fermentations under fed-batch conditions is proposed.

This goal is achieved with a microtiter plate having several cavities, some to hold nutrient solution and others to hold culture liquid, where each cavity of the microtiter plate provided to hold nutrient solution is connected by a channel to at least one other cavity of the microtiter plate, i.e., a cavity provided to hold culture liquid, and where a diffusion barrier which controls the kinetics of the release of the nutrients for fed-batch fermentations is placed in each channel.

Because a channel permeable to nutrients connects one cavity to at least one other cavity, the inventive microtiter plate can be used for screening under fed-batch conditions by filling the cavities with culture liquid and nutrient solution in such a way that each cavity of the microtiter plate filled with nutrient solution (nutrient cavity) is connected by the channel to at least one cavity of the microtiter plate filled with culture liquid (culture cavity).

The inventive microtiter plate makes it possible to screen a large number of strains, media, and products by fermentation under fed-batch conditions. The nutrient cavities can be filled with different nutrient solutions, so that the same microtiter plate can be used for different screening tasks. The nutrients may include, for example, various sources of C, N, or P. Inductors can also be added to the nutrient cavities.

The diffusion barrier in the channel between the cavity with the nutrient solution and the cavity or cavities with the culture liquid or liquids controls the kinetics of the release under fed-batch conditions. Depending on the properties of the diffusion barrier, the nutrients are released to the culture liquid at a faster or a slower rate.

In the simplest case, adjacent cavities of a microtiter plate are connected to each other in pairs by a channel. In this variant of the invention, each cavity with nutrient solution is assigned to a cavity with culture liquid. In the case of a conventional microtiter plate with 96 cavities, therefore, 48 assigned cavities serve as bioreactors for the fermentation, and 48 cavities serve as nutrient solution supply vessels.

In one embodiment of the invention, the channels proceeding from several cavities filled with culture liquid lead to a common cavity containing nutrient solution. In this case, this cavity containing nutrient solution supplies several culture cavities. If a large number of cavities filled with culture liquid are supplied from a single cavity with nutrient solution, the filling volume of the cavity for the nutrient solution is preferably greater than that of the cavities for the culture liquid. The cavities for the culture liquid are in this case preferably arranged around the cavity containing the nutrient solution.

It is especially preferable for three adjacent cavities to be connected to each other by channels, where two channels lead into one of the three cavities. This central cavity contains the nutrient solution, which is released into the adjacent cavities containing culture liquid through the two channels. The main advantage of this variant of the invention is that the cavity to which several channels lead does not need to have a shape and/or a filling volume which is different from that of the other cavities, which means that, to produce the inventive microtiter plate, it is possible to make use of plates with a standard matrix and a standard diameter for the cavities. In the case of a plate with 96 cavities, the present embodiment of the invention will have 64 cavities available for the culture liquid.

Under certain fermentation conditions, it can be advantageous for the diameter of the cavities for the nutrient solution to be smaller than the diameter of the cavities for the culture liquid. The higher surface tension resulting from the smaller diameter prevents the nutrient solution from rotating in the cavity after the shaking of the microtiter plate has begun. It is therefore possible to prevent the nutrient solution from running out over the edge of the cavity at the beginning of the fermentation process when the level of the liquid is at its highest.

The permeability of the diffusion barriers present in the channels is determined by their length, their cross section, and the nature of the material. If the nutrient is to be supplied slowly to the culture liquid during fermentation because the goal is, for example, to cultivate a microorganism with a slow growth rate, very small channel cross sections on the order of a millimeter would have be realized in the case of straight connecting channels. Such channels are very difficult to fabricate with high geometric reproducibility. In these cases, the course of the channel between the cavities is preferably not straight but rather curved. The use of curved and therefore longer channels makes it possible for these channels to have a larger and therefore easier-to-fabricate diameter. Another advantage which can be obtained from a long connecting channel which is not straight is that the nutrient feed into the culture cavity will begin only a certain period of time after the microtiter plate has been filled and the experiment has been started.

The channels between the cavities are filled at least partially, but preferably completely, with water-insoluble natural or synthetic polymers (hydrogel) as a diffusion barrier. The diffusion barrier seals off the connecting channel between the nutrient cavity and the culture cavity on the liquid side. A hydrogel is a polymer which contains water but is insoluble in water, the molecules of the polymer being linked chemically, for example, by covalent or ionic bonds or physically into a network. Especially as a result of their biocompatibility and mechanical properties which are similar to those of tissue, they are being used increasingly in the field of biotechnology. Alternatively, the diffusion barrier can consist of a microporous material of plastic, glass, ceramic, or metal.

The use of polyacrylamide as a diffusion barrier has been found to be especially advantageous. Polyacrylamide is the polymeric form of acrylamide. The polymerization of acrylamide to polyacrylamide is brought about by a chain reaction. This reaction can be started by, for example, ammonium persulfate (APS) as a radical and catalyzed by TEMED (tetramethylethylenediamine). A gel-like matrix, that is, the polyacrylamide, is thus formed. The natural and synthetic polymers listed below have also been found to be advantageous:

cellulose, i.e., polysaccharides such as alginates;

gelan, carrageenan, chitosan, and their derivatives;

polysiloxanes and their derivatives;

polyacrylic acid and its derivatives;

polycarbonates and their derivatives;

polyolefins and their derivatives;

polycarboxylic acids and their derivatives;

polyethers and their derivatives;

polyesters and their derivatives;

polyamines and their derivatives;

polyamides and their derivatives;

polysulfones and their derivatives;

polyurethanes and their derivatives;

polyvinyls and their derivatives, especially polyvinyl alcohols; and copolymers of the cited polymers and derivatives obtained by modification.

The diffusion barrier ensures a controlled and reproducible transfer of nutrients to the culture liquid, where the release kinetics are determined in such a way that both an excess and a deficiency of nutrient is avoided. Depending on the type of fermentation, the culture liquid is supplied with a specific nutrient concentration over a period ranging from a few hours to a few weeks.

The permeability of the diffusion barrier for nutrients from carbon-based nutrient solutions is:

2.5-250 $g_{nutrient}/(L_{culture\ volume} \times h_{total\ culture\ time})$] or 0.08-8 $mol_{carbon\ atoms}/(L_{culture\ volume} \times h_{total\ culture\ time})$, preferably 12-72 $g_{nutrient}/(L_{culture\ volume} \times h_{total\ culture\ time})$] or 0.4-2.4 $mol_{carbon\ atoms}/(L_{culture\ volume} \times h_{total\ culture\ time})$ In the case of nitrogen sources, calculated on the basis of atoms, permeabilities which are less by a factor of 0.2 than those for carbon sources have been found to be reliable. In the case of phosphorus sources, permeabilities less by a factor of 0.01, and, in the case of sulfur sources, permeabilities less by a factor of 0.005 have proven suitable.

The introduction of the diffusion barrier into the channels of the inventive microtiter plate is carried out, for example, by adding a drop of an as-yet-unsolidified hydrogel solution into one of the two cavities connected by a channel. A pipetting robot can be used for this purpose. The unsolidified hydrogel is drawn by capillary forces into the channel and solidifies there. It can be advantageous for this purpose to hydrophilize the channels (and the cavities) by means of, for example, a chemical treatment or a plasma treatment before the introduction of the as-yet-unsolidified hydrogel solution. Another production method consists in centrifuging the microtiter plate to introduce the as-yet-unsolidified hydrogel into the channels. This method is explained in greater detail below on the basis of the figures.

The inventive microtiter plate can be produced at especially low cost by making use of the components of a conventional microtiter plate consisting of a bottom plate and a cavity plate. In this embodiment of the invention, the inventive microtiter plate comprises a known bottom plate and cavity plate with hollow cylindrical or slightly conical passages, where the bottom plate and the cavity plate are connected to each other in a liquid-tight manner. To this extent, the design is the same as that of the previously mentioned known two-part microtiter plate. To produce the inventive microtiter plate, furthermore, groove-like recesses are introduced into the surface of the bottom plate forming the bottoms of the cavities. These recesses are partially closed off liquid-tight by areas of the cavity plate located between the passages. The channels between the cavities are thus obtained. To ensure that the connection between two cavities formed by the channel is permeable to the substance in question, the recesses extend far enough through the bottom plate that each end projects by a certain amount underneath one of the passages in the cavity plate. The groove-like recesses can be introduced into the known bottom plate by milling or at low cost by hot stamping. It is also possible, however, to provide the groove-like recesses during the original injection-molding or extrusion process used to produce the bottom plate.

If the channels are to be filled by centrifuging the inventive microtiter plate, the recess stamped into the bottom plate is preferably designed in accordance with the features of Subclaim 16.

To allow the on-line monitoring of the culture liquids during the shaking of the microtiter plate, at least part of the bottoms of at least the culture cavities is made of transparent material. If the microtiter plate is assembled from a bottom plate and a cavity plate, the bottom plate will preferably be made completely of transparent material (such as polystyrene, polycarbonate, polymethyl methacrylate, their derivatives or blends, or possibly of glass or quartz glass) to allow on-line monitoring. The bottom plate can be very thin in the area of the cavities, e.g., in the range between 10 μm and 500 μm, to guarantee good transmission of short-wavelength light (<280 nm).

A central advantage of the inventive microtiter plate is that the cavities can be filled by pipet in automated fashion. Conventional pipetting robots can be used for this purpose. The microtiter plate is covered in sterile fashion either by means of conventional self-adhering films or by means of a removable cover.

It is possible with the inventive microliter plate not only to select the nutrient solution and to specify the release kinetics but also to supply the nutrient solution to the nutrient cavities a certain period of time after the start of fermentation. It is possible as a result effectively to avoid an excess of nutrient in the culture liquid during the initial phase. The time at which the nutrient solution first starts to be supplied can be determined by on-line monitoring of the culture liquids.

Additional nutrient solution with a different concentration, furthermore, can also be added to each of the nutrient solution-filled cavities after a certain period of time. First, for example, a small amount of nutrient solution of low concentration can be added to the nutrient cavity, and this can then be supplemented at a later time with additional portions of nutrient solution of higher concentration. As a result of this measure, the driving concentration gradient between the nutrient solution and the culture liquid is increased. Thus the transfer of nutrients by diffusion can be adapted to the increasing demands of a growing culture.

In the normal case, the level of nutrient solution in a nutrient cavity and the level of culture fluid in the culture cavity connected to the former by a channel are equal at the beginning of the fermentation. In some applications, however, the nutrient solution has a very high concentration. As a result, a pronounced osmotic pressure gradient can develop, which leads to a diffusion of water out of the culture liquid and into the nutrient solution. This is undesirable, because the level of the culture liquid falls and the level of the nutrient solution rises. In these cases, it can therefore be advantageous to make the level of the nutrient solution higher than the level of the culture liquid at the beginning of the fermentation. The different hydrostatic pressures counteract the osmotic pressure, and the diffusion of water out of the culture liquid, through the diffusion barrier, and into the nutrient solution is decreased.

The invention is explained in groater detail below on the basis of the figures:

DETAILED DESCRIPTION OF THE PRESENTLY PREFERRED EMBODIMENTS

Figure 1A:
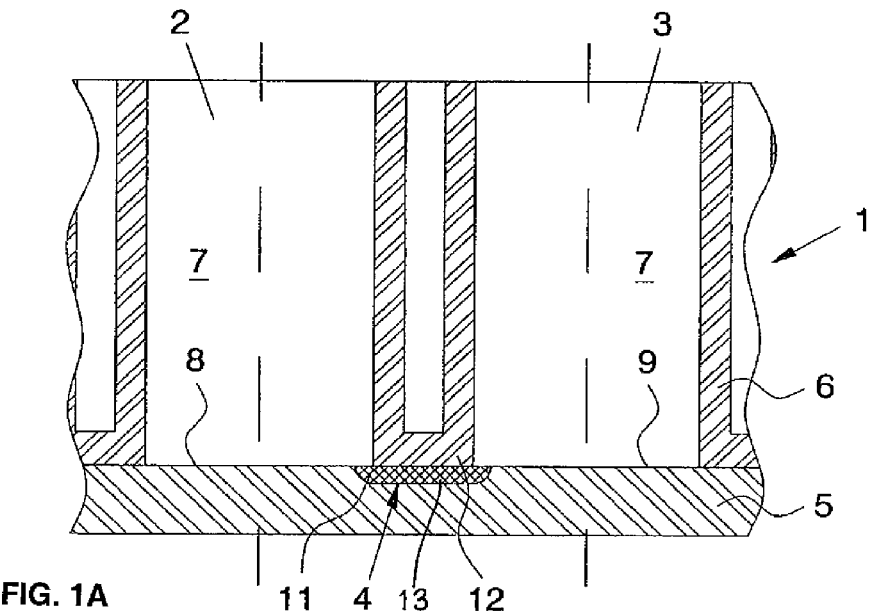
FIG. 1A is a cross-section taken along line A-A in FIG. 1.
Figure 1:
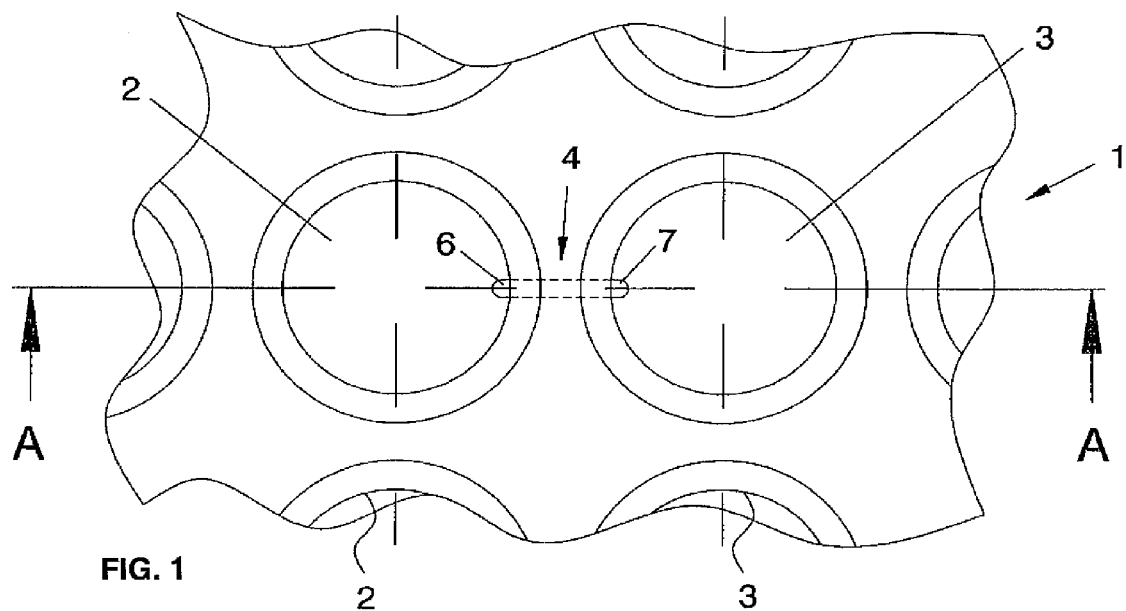
FIG. 1 shows a partial plan view of an inventive microtiter plate.

FIG. 1 shows part of an inventive microtiter plate 1 with cavities 2, 3, which are connected to each other by a channel 4. The microtiter plate 1 is formed by a bottom plate 5 and a cavity plate 6, which has hollow cylindrical or slightly conical passages 7 extending between the opposing parallel surfaces of the cavity plate 6, where the bottom plate 5 and the cavity plate 6 are joined to each other in a liquid-tight manner. Suitable joining methods include, for example, laser welding; friction welding; ultrasonic welding; solvent bonding; the application of adhesive onto the surfaces to be bonded by X-Y traversing units using air-pressure dosing, syringe dosing, or piezoelectric dosing; by rolling on or stamping on the adhesive, or by the use of prestructured double-sided adhesive films.

Elongated, groove-like recesses 11 are introduced into the surface of the bottom plate 5 where the bottoms 8, 9 of the cavities 2, 3 are located. These recesses are partially closed off from above by the areas 12 of the cavity plate 6 located between the passages 7. The web-like areas 12 between the passages 7 cooperate with the recesses 11 to form the channels 4, which extend between the bottoms 8, 9 of the cavities 2, 3. The cavity 2, for example, serves to hold the nutrient solution, whereas the cavity 3 holds the culture liquid. A diffusion barrier 13 is placed in the channel 4.

Figure 2A:
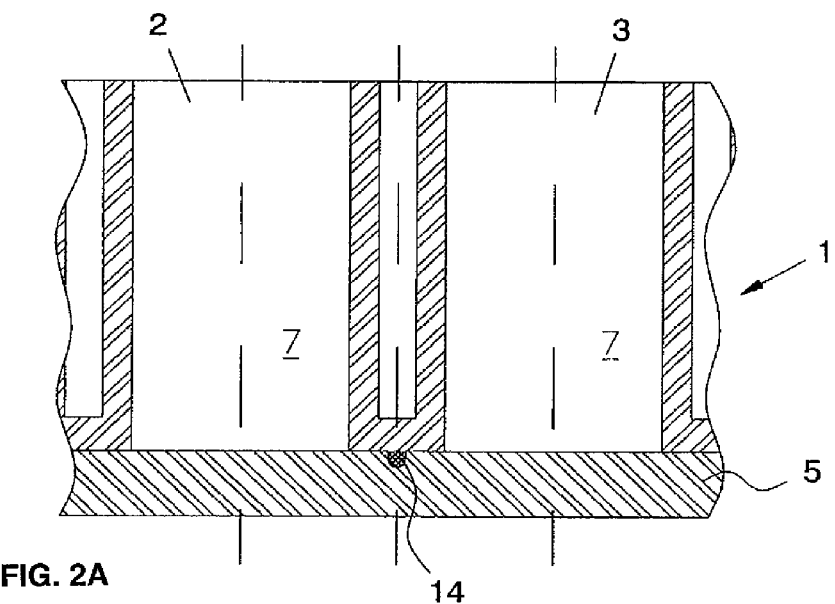
FIG. 2A is a cross-section taken along line A-A in FIG. 2.
Figure 2:
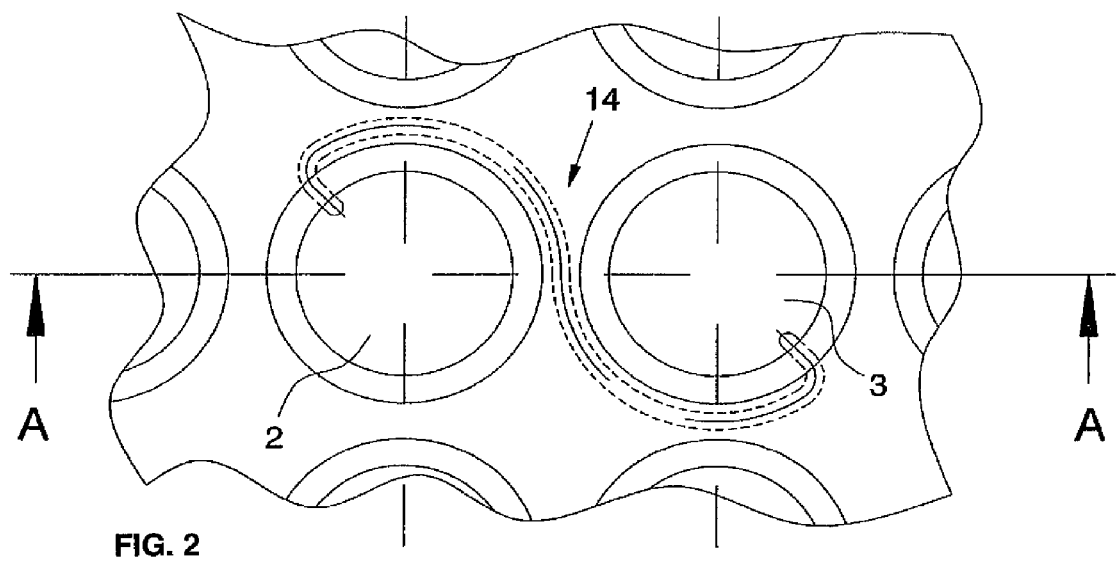
FIG. 2 shows a partial plan view of a second embodiment of an inventive microtiter plate with curved channels.

The diagram of the microtiter plate in FIG. 2 is largely the same as that of the embodiment shown in FIG. 1. To the extent that they are the same, reference is made to the explanation of FIG. 1. A difference is present only with respect to the length of the channel 14 extending between the cavities 2, 3. In contrast to FIG. 1, the channel 14 connects the two cavities not by the shortest route but rather by a curved route, so that the channel has a greater length. Under the assumption that the same type of material is used for the diffusion barrier 13, the greater length of the channel results in a higher overall diffusion resistance, which can be desirable for bringing about a slower and/or time-delayed addition of the nutrients.

Figure 3A:
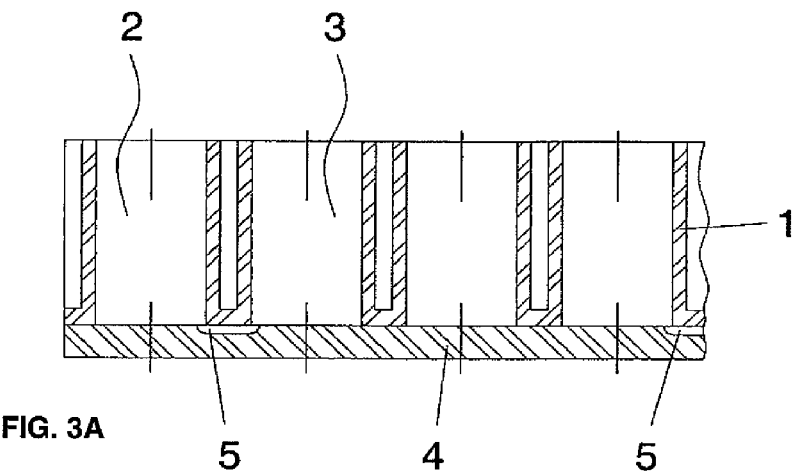
FIG. 3A is a cross-section taken along line A-A in FIG. 3.
Figure 3:
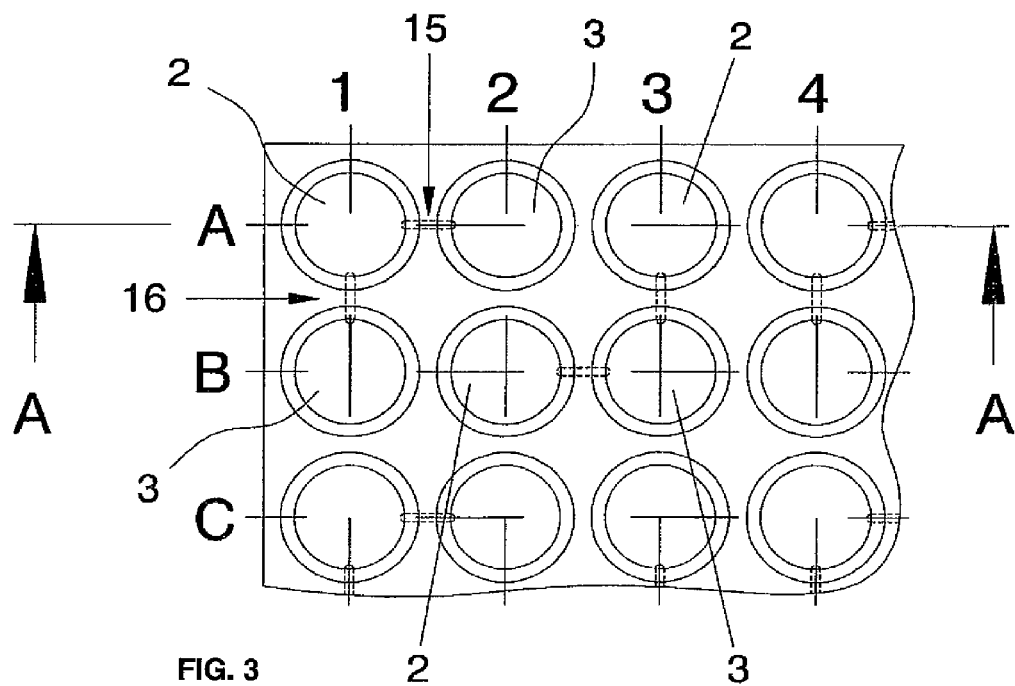
FIG. 3 shows a partial plan view of a third embodiment of the inventive microtiter plate where three adjacent cavities are connected to each other by channels.
Figure 3B:
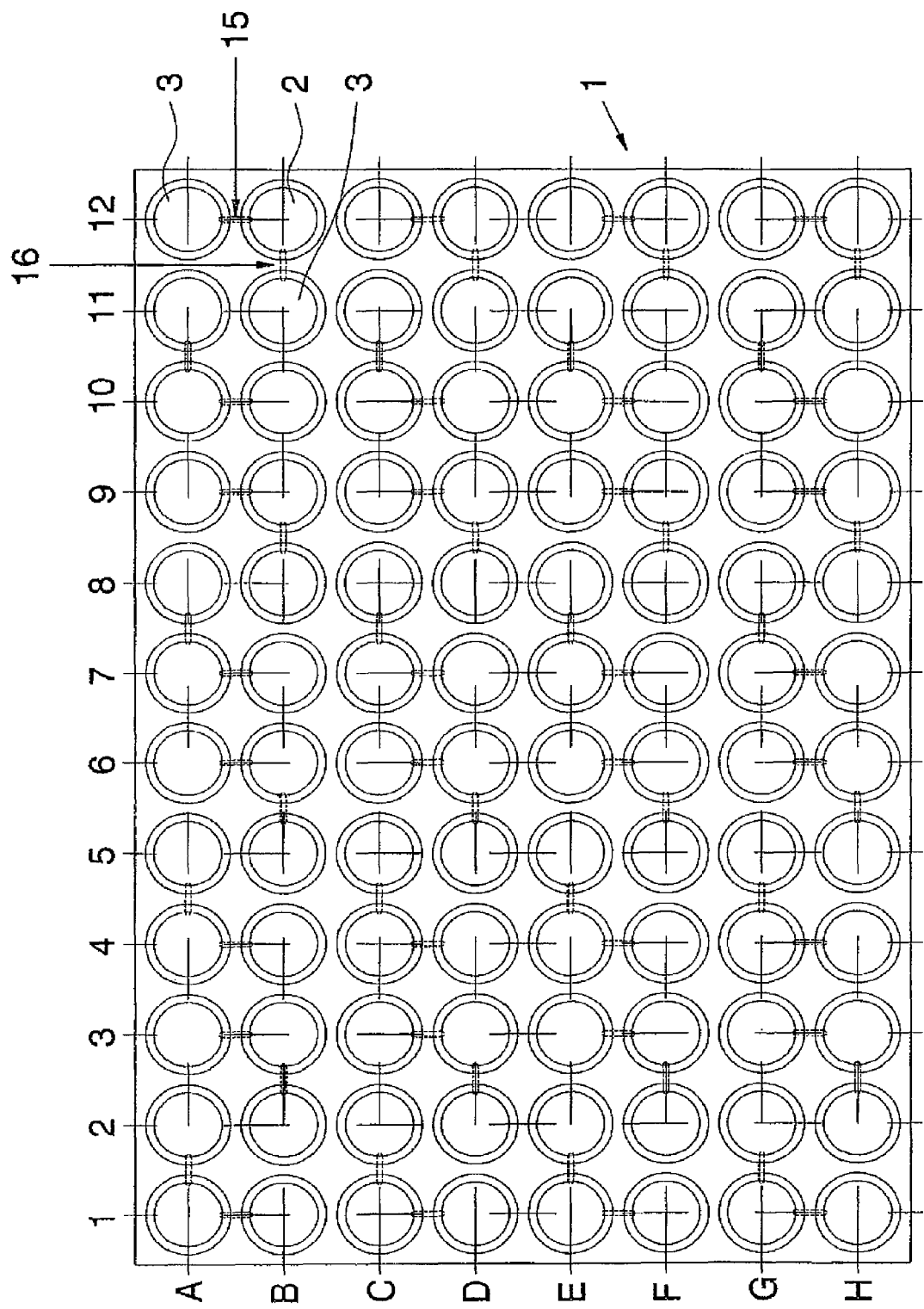
FIG. 3B is an overall plan view of the third embodiment.

FIGS. 3, 3A and 3B show a complete inventive microliter plate, in which three adjacent cavities 2, 3 are connected to each other by two channels 15, 16, where the two channels 15, 16 lead to the central cavity 2. The central cavity 2 is filed with nutrient solution, whereas the two outer cavities 3 are filled with culture liquid. A diffusion barrier 13 is present in each channel 15, 16. The two cavities 3 filled with culture liquid are fed with nutrients from the central cavity 2 via the channels 15, 16. This embodiment offers the advantage that 64 cavities can be cultivated simultaneously with culture liquid on the microtiter plate with 96 cavities shown in FIG. 3, where, in the embodiment according to FIGS. 1 and 2, only 48 cavities can be used for cultures.

Figure 4:
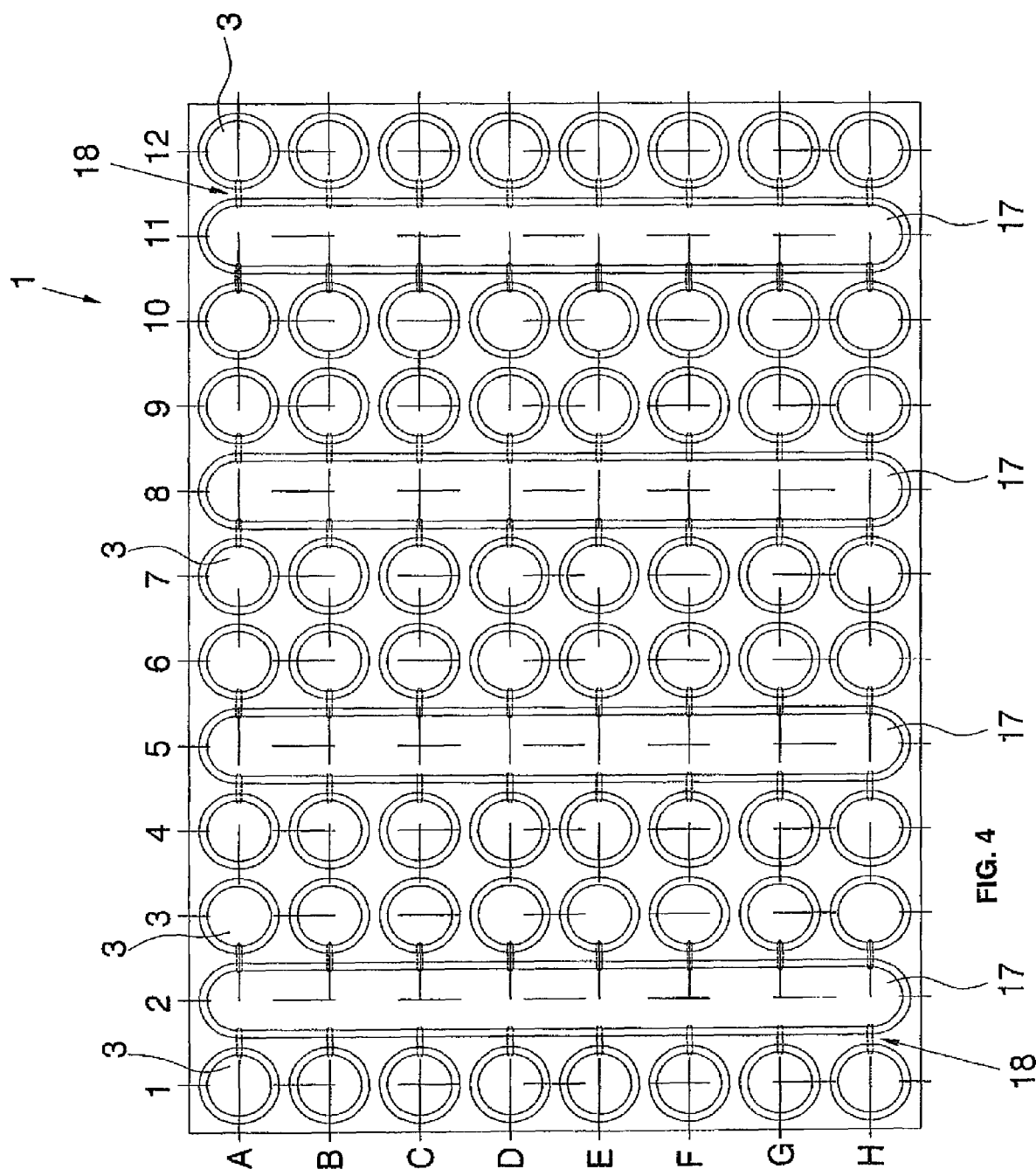
FIG. 4 shows a view of a fourth embodiment of an inventive microtiter plate, where the channels of a plurality of cavities lead to a elongated central cavity.

FIG. 4 shows another variant of the inventive mocrotiter plate, in which 16 culture liquid-filled cavities 3 are supplied with nutrients from one cavity 17. The channels 18 of the 16 cavities 3 lead to the cavity 17, which extends across the entire width of the microtiter plate 1 between two columns of cavities 3. A diffusion barrier 13 is present in each of the channels 18 between the cavities 3 and the elongated cavity 17. With this embodiment, as also in the case of the embodiment shown in FIG. 3, it is possible to use 64 cavities for cultures, but only 4 nutrient cavities need to be filled instead of the 32 cavities in FIG. 3. This saves time when setting up the experiment.

Figure 5A:
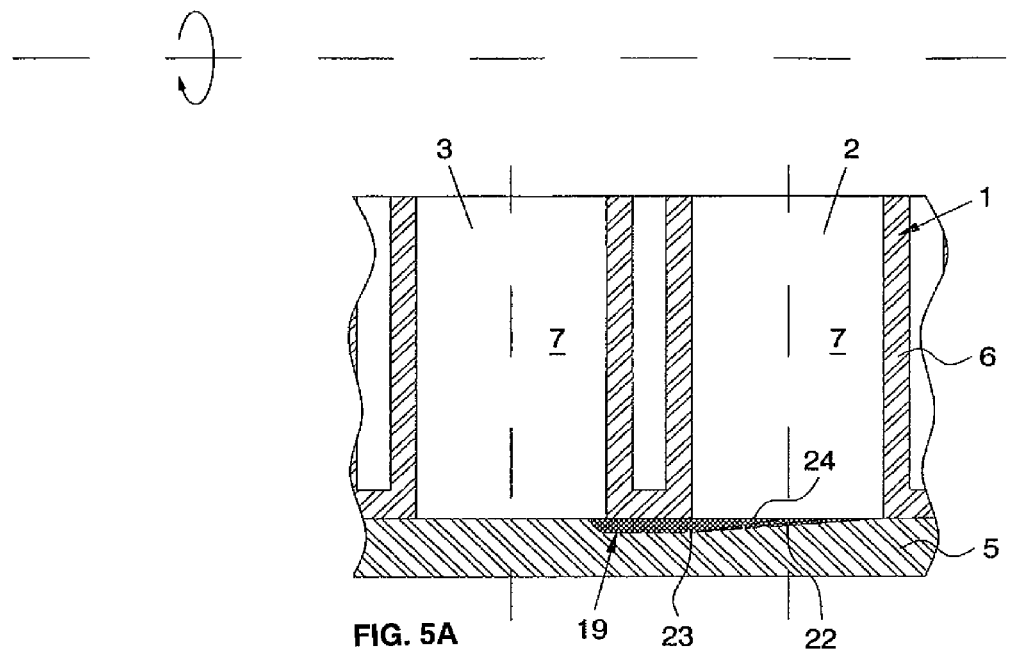
FIG. 5A is a cross-section taken along line A-A in FIG. 5.
Figures 5, 5B:
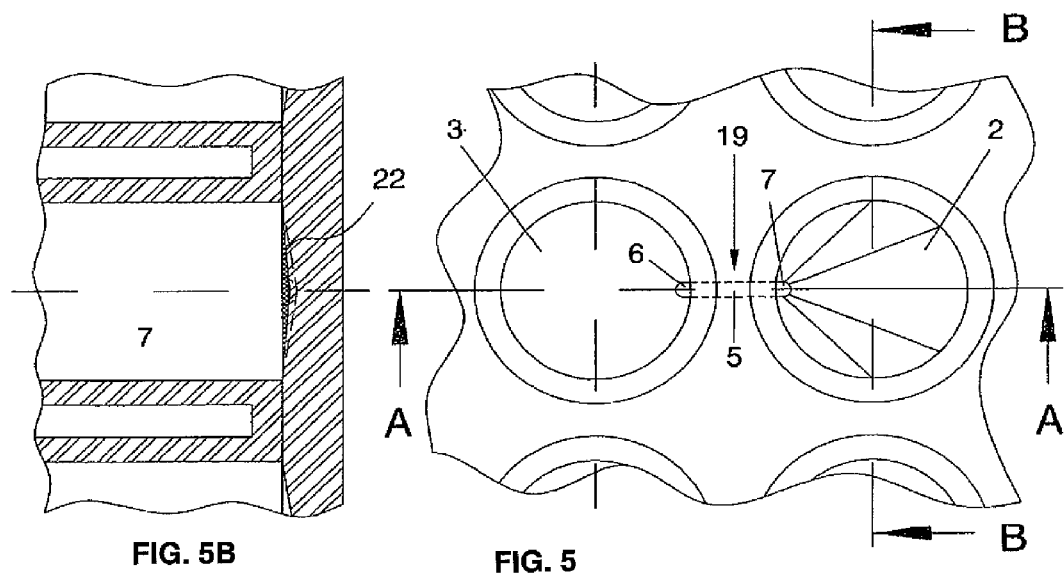
FIG. 5 shows a partial view of a fifth embodiment of an inventive microtiter plate with the channels being designed in a way which is advantageous in terms of production technology.
FIG. 5B is a cross-section taken along line B-B in FIG. 5.

The microtiter plate 1 shown in a partial view in FIG. 5 is largely the same as the microtiter plate according to FIG. 1. To this extent, reference can be made to the explanation of FIG. 1. Two cavities 2, 3 are connected to each other by a channel 19, which again is formed by a groove-like recess in the bottom plate 5. In contrast to FIG. 1, one end of the groove-like recess expands underneath the passage 7 in the cavity plate 6. The depth of the expanded area 22, as can be seen in the cross sections A-A and B-B, decreases as the recess proceeds from the point 23 of the groove-like recess of the channel 19 at which the expansion begins. The bottom 24 of the cavity 2 therefore slopes down toward the starting point 23. The design of the bottom 24 offers technical advantages with respect to production during the filling of the channel 19 with the hydrogel which forms the diffusion barrier 13. To fill the channel, a pipetting robot, for example, applies an as-yet-unsolidified hydrogel solution onto the bottom 24 of the cavity 2. Then the entire microtiter plate 1 is spun in a centrifuge around the axis of rotation indicated in the cross section A-A. As a result of centrifugal force, the as-yet-unsolidified hydrogel solution is spun into the channel 19. The quantity of hydrogel solution is preferably calculated in such a way that, after centrifuging, a layer of hydrogel is obtained which is level with the surface of the bottom plate 5. This ensures that the form of the diffusion barrier and the size of its contact surfaces with the nutrient solution/culture liquid are precisely defined. In the case of the embodiment shown here, the cavity 2 is preferably the nutrient cavity, and the cavity 3 is the culture cavity. This guarantees that the cultures can be monitored through an optically transparent, defect-free bottom by means of an on-line monitoring system.

The invention claimed is:

1. Microtiter plate comprising:
   a top surface;
   a plurality of first cavities which open on the top surface, wherein the first cavities are provided for holding a nutrient solution;
   a plurality of second cavities which open on the top surface, wherein the second cavities are provided for holding a culture liquid;
   a plurality of channels, each of said channels respectively connecting one of said first cavities to at least one of said second cavities; and
   a diffusion barrier provided in each of said channels, the diffusion barrier being designed to control the release of nutrients in a fed-batch manner from a nutrient solution in the first cavity to a culture liquid in the at least one second cavity such that the diffusion barrier prevents both an excess and a deficiency of nutrients in the at least one second cavity, wherein each said diffusion barrier seals said each of said channels, and the diffusion barrier having a permeability determined by a length, cross-section, and nature of a material of the diffusion barrier, the permeability selected from the group consisting of
   a permeability to carbon sources in the range of 2.5-250 g carbon source/($L_{culture\ volume} \times h_{total\ culture\ time}$)
   a permeability to nitrogen sources in the range of 0.016-1.6 mol nitrogen atoms/($L_{culture\ volume} \times h_{total\ culture\ time}$)
   a permeability to phosphorous sources in the range of 0.0008-0.08 mol phosphorus atoms/($L_{culture\ volume} \times h_{total\ culture\ time}$), and
   a permeability to sulfur sources in the range of 0.0004-0.04 mol sulfur atoms/($L_{culture\ volume} \times h_{total\ culture\ time}$).

2. The microtiter plate of claim 1 wherein the diffusion barrier is designed to release an excess of nutrients in an initial phase, and to limit the release of nutrients in a subsequent phase.

3. The microtiter plate of claim 1 wherein said diffusion barrier seals the each of said channels in a liquid-tight manner.

4. The microtiter plate of claim 1 wherein the diffusion barrier has the permeability to carbon sources in the range of 2.5-250 g carbon source/($L_{culture\ volume} \times h_{total\ culture\ time}$).

5. The microtiter plate of claim 1 wherein the diffusion barrier has the permeability to nitrogen sources in the range of 0.016-1.6 mol nitrogen atoms/($L_{culture\ volume} \times h_{total\ culture\ time}$).

6. The microtiter plate of claim 1 wherein the diffusion barrier has the permeability to phosphorous sources in the range of 0.0008-0.08 mol phosphorus atoms/($L_{culture\ volume} \times h_{total\ culture\ time}$).

7. The microtiter plate of claim 1 wherein the diffusion barrier has the permeability to sulfur sources in the range of 0.0004-0.04 mol sulfur atoms/($L_{culture}$volume$\times h_{total\ culture\ time}$).

8. The microtiter plate of claim 1 wherein each said first cavity is connected to only one adjacent said second cavity.

9. The microtiter plate of claim 1 wherein each said first cavity is connected to a plurality of adjacent said second cavities.

10. The microtiter plate of claim 9 wherein each of said cavities has a shape and a volume, wherein at least one of said shape and said volume of each said first cavity is different from at least one of said shape and said volume of said second cavities.

11. The microtiter plate of claim 1 wherein the channels are straight.

12. The microtiter plate of claim 1 wherein the channels are curved.

13. The microtiter plate of claim 1 wherein the diffusion barrier comprises polyacrylamide at least partially filling each said channel.

14. The microtiter plate of claim 1 comprising:
a cavity plate having a plurality of through passages; and
a bottom plate which is received against the cavity plate to close the passages, thereby forming bottoms of respective said cavities, the bottom plate having a plurality of groove-like recesses which connect adjacent said cavities to form said channels, each said recess have opposed ends which extend into adjacent said bottoms.

15. The microtiter plate of claim 14 wherein one of said ends of each said recess expands and decreases in depth as it extends into said bottom.

16. The microtiter plate of claim 14 wherein at least part of said bottoms consists of a transparent material.

17. The microtiter plate of claim 16 wherein the bottom plate consists of a transparent material.

18. A fermentation method comprising:
providing the microtiter plate of claim 1 having a plurality of first cavities and a plurality of second cavities, wherein each said first cavity is connected to at least one said second cavity by a channel having a diffusion barrier designed to control the release of nutrients from a nutrient solution in the first cavity to a culture liquid in the at least one second cavity;
at least partially filling the first cavities with a nutrient solution; and
at least partially filling the second cavities with a culture liquid, wherein the diffusion barrier prevents both an excess and a deficiency of nutrients in the second cavities, wherein said diffusion barrier seals said channel, and wherein the diffusion barrier has a permeability selected from the group consisting of
a permeability to carbon sources in the range of 2.5-250 g carbon source/($L_{culture\ volume} \times h_{total\ culture\ time}$)
a permeability to nitrogen sources in the range of 0.016-1.6 mol nitrogen atoms/($L_{culture\ volume} \times h_{total\ culture\ time}$)
a permeability to phosphorous sources in the range of 0.0008-0.08 mol phosphorus atoms/($L_{culture\ volume} \times h_{total\ culture\ time}$), and
a permeability to sulfur sources in the range of 0.0004-0.04 mol sulfur atoms/($L_{culture\ volume} \times h_{total\ culture\ time}$).

19. The fermentation method of claim 18 wherein the first and second cavities are filled by pipets in an automated manner.

20. The fermentation method of claim 18 further comprising shaking the microtiter plate during fermentation.

21. The fermentation method of claim 18 wherein the nutrient solution is added to the first cavities for a time after fermentation begins.

22. The fermentation method of claim 21 wherein the nutrient solution has a concentration which is varied while it is being added.

* * * * *